United States Patent [19]
Sertich

[11] Patent Number: 5,846,077
[45] Date of Patent: *Dec. 8, 1998

[54] DENTAL SCALER AND VIBRATORY TRANSDUCER THEREFOR

[76] Inventor: Anthony T. Sertich, 137 MacIntyre La., Allendale, N.J. 07401

[ * ] Notice: The term of this patent shall not extend beyond the expiration date of Pat. No. 5,779,473.

[21] Appl. No.: 970,687

[22] Filed: Nov. 14, 1997

Related U.S. Application Data

[63] Continuation-in-part of Ser. No. 766,674, Dec. 13, 1996, Pat. No. 5,779,473.
[51] Int. Cl.⁶ .............................. A61C 1/07; A61C 3/08; B01F 11/00
[52] U.S. Cl. ............................................ 433/120; 366/126
[58] Field of Search ...................................... 433/118, 120, 433/124, 86, 119; 366/125, 126, 124

[56] References Cited

U.S. PATENT DOCUMENTS

| | | | |
|---|---|---|---|
| 2,480,603 | 8/1949 | Peterson . | |
| 2,921,372 | 1/1960 | Bodine, Jr. | 433/119 |
| 3,444,622 | 5/1969 | Mills et al. . | |
| 3,553,841 | 1/1971 | Austin, Jr. . | |
| 4,260,380 | 4/1981 | Nash . | |
| 4,427,384 | 1/1984 | Sertich | 433/120 |
| 4,453,919 | 6/1984 | Takeshita | 433/120 |
| 5,035,510 | 7/1991 | Fallows et al. | 366/126 |
| 5,190,456 | 3/1993 | Hasegawa | 433/120 |

*Primary Examiner*—Cary E. O'Connor
*Attorney, Agent, or Firm*—Arthur Jacob

[57] ABSTRACT

An air-driven dental scaler has a scaling tool vibrated at a high frequency and low amplitude by a vibratory transducer having a ball within a chamber, a race in the chamber, and air inlets and air outlets arranged for admitting air under pressure into the chamber and directing the air toward the ball adjacent one of the opposite poles of the ball, the relative dimensions of the chamber and the ball providing a relatively small clearance between the ball and the chamber for enabling relatively high speed rotation of the ball within the race in the chamber, in response to the passage of the air under pressure through the inlets into the chamber and through the outlets out of the chamber, and the concomitant transmission of relatively high frequency, low amplitude vibrational energy from the rotating ball to the scaling tool.

26 Claims, 4 Drawing Sheets

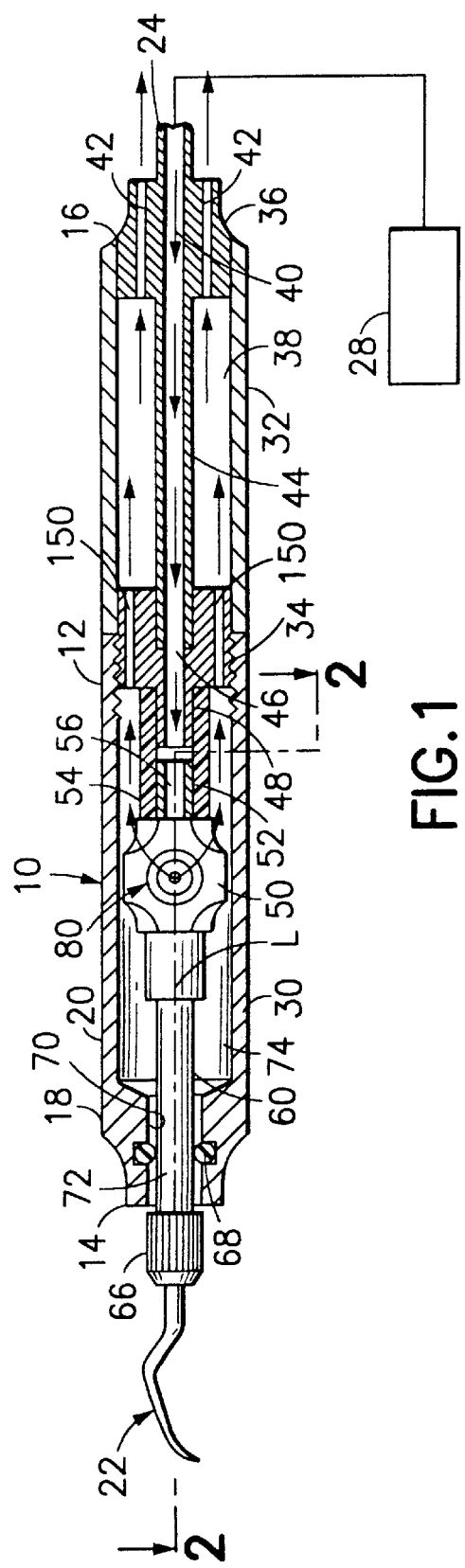
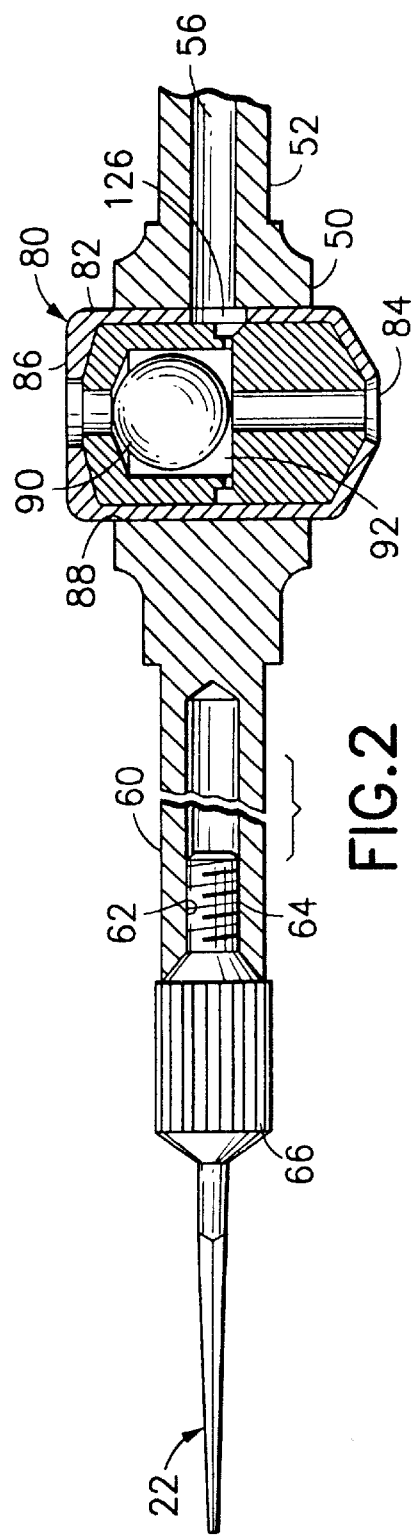

DENTAL SCALER AND VIBRATORY TRANSDUCER THEREFOR

This is a continuation-in-part of application Ser. No. 08/766,674, filed Dec. 13, 1996, now U.S. Pat. No. 5,779,473.

The present invention relates generally to dental scalers and to vibratory transducers suitable for use in dental scalers, and pertains, more specifically, to a dental scaler and to an air-driven vibratory transducer for producing high frequency, low amplitude vibrational energy to be transmitted to the scaling tool of the dental scaler.

In my earlier patents, U.S. Pat. Nos. Re. 29,687 and 4,427,384, I disclosed air-driven dental scalers which provide several advantages over previously available dental scalers. In particular, my earlier dental scalers have relatively few moving parts, are mechanically uncomplicated and provide efficient transfer of vibrational energy to a dental scaling tool, while relatively little vibration is transferred to the handle of the instrument.

The dental scaler of the present invention incorporates a mechanical vibratory transducer of improved design and construction for producing high frequency, low amplitude vibrational energy readily transmitted to the scaling tool of the instrument. As such, the present invention meets several objectives and attains several advantages, some of which are summarized as follows: Provides an air-driven vibratory dental scaler which is capable of operating at frequencies significantly higher than those attained by my earlier dental scalers; enables operation of a dental scaler at low amplitudes of vibration, with increased power; operates at lower noise levels than my earlier dental scalers; provides an instrument which is compact and is relatively simple in design and construction; provides a dental scaler which is more efficient in use and is more comfortable from the standpoint of both the dental operator and the patient; provides a vibratory transducer for use in various other implements for enabling the construction of more effective implements; enables the construction of a vibratory transducer of simplified and economical construction.

The above objects and advantages, as well as further objects and advantages, are attained by the present invention which may be described briefly as a dental scaler having a scaling tool to be vibrated at a high frequency and low amplitude by a fluid under pressure, the dental scaler comprising: an outer tubular housing extending along a longitudinal axis between opposite ends; a vibratory transducer within the outer tubular housing; coupling means for coupling the scaling tool to the vibratory transducer; resilient support means for supporting the vibratory transducer within the outer tubular housing; the vibratory transducer comprising: an inner housing having a chamber including a peripheral wall extending between opposite first and second chamber ends; an essentially spherical rotor within the chamber, the rotor having a diameter, a polar axis extending along the diameter between opposite poles, and an equator intermediate the opposite poles; a race in the peripheral wall of the chamber, the race being located intermediate the first and second chamber ends and juxtaposed with the equator of the rotor; at least two fluid inlets located adjacent the first chamber end and juxtaposed with one of the opposite poles of the rotor for admitting the fluid under pressure into the chamber and directing the fluid toward the rotor adjacent the one of the opposite poles; and at least one fluid outlet aligned essentially with the polar axis of the rotor for exhausting from the chamber the fluid admitted into the chamber; the relative dimensions of the peripheral wall of the chamber and the diameter of the rotor providing a relatively small clearance between the rotor and the peripheral wall of the chamber for enabling relatively high speed rotation of the rotor within the race in the chamber, in response to the passage of the fluid under pressure through the inlets into the chamber and through the outlet out of the chamber, and the concomitant transmission of relatively high frequency, low amplitude vibrational energy from the rotating rotor to the inner housing and to the scaling tool.

In addition, the invention includes a vibratory transducer for providing high frequency, low amplitude vibrational energy in response to a fluid under pressure, the vibratory transducer comprising: a housing having a chamber including a peripheral wall extending between opposite first and second chamber ends; an essentially spherical rotor within the chamber, the rotor having a diameter, a polar axis extending along the diameter between opposite poles, and an equator intermediate the opposite poles; a race in the peripheral wall of the chamber, the race being located intermediate the first and second chamber ends and juxtaposed with the equator of the rotor; at least two fluid inlets located adjacent the first chamber end and juxtaposed with one of the opposite poles of the rotor for admitting the fluid under pressure into the chamber and directing the fluid toward the rotor adjacent the one of the opposite poles; and at least one fluid outlet aligned essentially with the polar axis of the rotor for exhausting from the chamber the fluid admitted into the chamber; the relative dimensions of the peripheral wall of the chamber and the diameter of the rotor providing a relatively small clearance between the rotor and the peripheral wall of the chamber for enabling relatively high speed rotation of the rotor within the race in the chamber, in response to the passage of the fluid under pressure through the inlets into the chamber and through the outlet out of the chamber, and the concomitant transmission of relatively high frequency, low amplitude vibrational energy from the rotating rotor to the housing.

The invention will be understood more fully, while still further objects and advantages will become apparent, in the following detailed description of preferred embodiments of the invention illustrated in the accompanying drawing, in which:

FIG. 1 is a longitudinal cross-sectional view of a dental scaler utilizing a vibratory transducer constructed in accordance with the present invention;

FIG. 2 is an enlarged longitudinal cross-sectional view of a portion of the dental scaler, taken along line 2—2 of FIG. 1;

Figure 3:
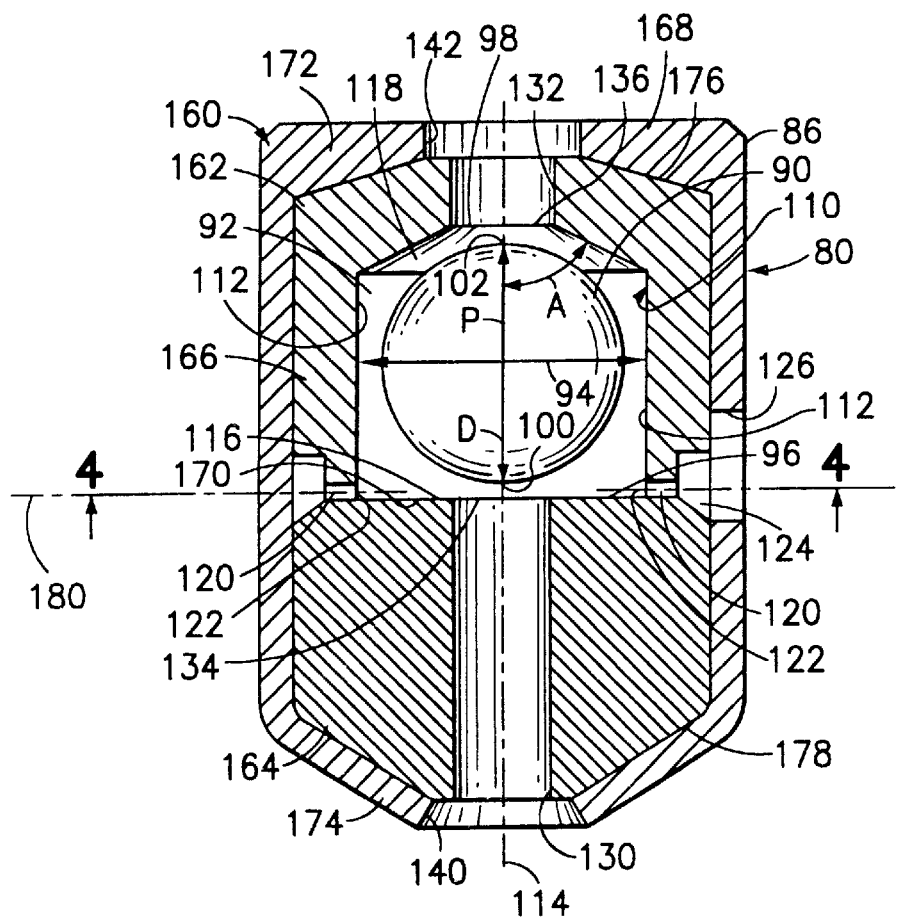
FIG. 3 is a further enlarged longitudinal cross-sectional view of the vibratory transducer.

Referring now to the drawing, and especially to FIGS. 1 and 2 thereof, a dental scaler constructed in accordance with the invention is shown at 10 and is seen to include an outer housing 12 extending longitudinally along a longitudinal axis L between a forward end 14 and a rearward end 16. Outer surface 18 of the housing 12 includes a finger grip portion 20 by which a dental operator may grasp the implement during use. A typical scaling tool 22 is shown at the forward end 14, while a nipple 24 is provided at the rearward end 16 for enabling the dental scaler 10 to be coupled to a supply 28 of fluid under pressure, the fluid being air, usually available at the point of use of the implement.

Housing 12 is seen to be constructed in the form of a segmented outer tubular member including a forward tubular segment 30 and a rearward tubular segment 32, the forward and rearward tubular segments 30 and 32 being coupled together by a threaded coupling member 34. Nipple 24 is unitary with a rear fitting 36 secured at the rearward end of the rearward tubular segment 32, the threaded coupling member 34 and the rear fitting 36 being placed at the forward and rearward ends, respectively, of the interior 38 of the rearward tubular segment 32.

The rear fitting 36 includes a rear air feed passage 40 and rearward air exhaust passages 42. An air tube 44 is unitary with the rear fitting 36 and enters the coupling member 34 so that rear air feed passage 40 communicates with an intermediate air feed passage 46 which extends longitudinally through a neck 48 projecting forward along the coupling member 34. A forward fitting 50 includes a rearwardly projecting neck 52, and a tubular coupling member 54 constructed of a resilient elastomeric material is fitted over the necks 48 and 52 to couple the forward fitting 50 with the coupling member 34. At the same time, coupling member 54 completes communication between the intermediate air feed passage 46 and a forward air feed passage 56 extending longitudinally through the neck 52. Forward fitting 50 further includes a longitudinally extending shaft 60 having a threaded socket 62 at the forward end thereof, and the threaded socket 62 receives a complementary threaded stud 64 which projects from a collar 66 on the scaling tool 22 and is threaded into the socket 62 to serve as coupling means for coupling and securing the scaling tool 22 to the shaft 60. A ring 68 of resilient elastomeric material supports shaft 60 within a bore 70 in the forward tubular segment 30. Bore 70 has an inside diameter slightly greater then the outside diameter of the portion 72 of shaft 60 passing through the bore 70, for purposes to be described below, and ring 68 seals the forward end of the interior 74 of the forward tubular segment 30.

A vibratory transducer 80 is mounted in the forward fitting 50 and, as best seen in FIG. 2, includes a housing 82 extending between a first end 84 and a second end 86. Housing 82 is affixed within forward fitting 50 so as to be integral therewith, as by a press fit between the housing 82 and a complementary bore 88 in the forward fitting 50, housing 82 constituting an inner housing relative to the outer housing 12. A rotor in the form of an essentially spherical ball 90 is placed within a chamber 92 in the housing 82, the chamber 92 being essentially cylindrical, with a cylindrical diameter 94, and having opposite first and second ends 96 and 98 (see FIG. 3).

Figure 4:
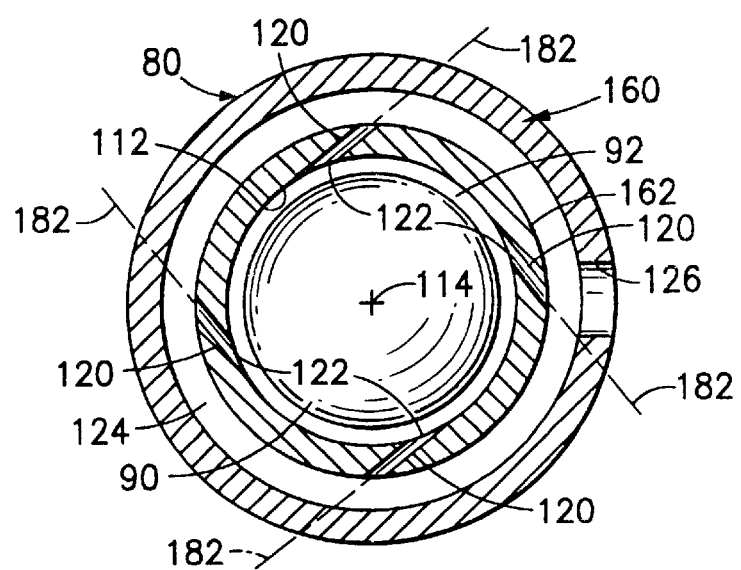
FIG. 4 is a cross-sectional view taken along line 4—4 of FIG. 3.

Turning now to FIGS. 3 and 4, as well as to FIGS. 1 and 2, ball 90 has a diameter D and a polar axis P which extends along the diameter D between opposite poles 100 and 102 of the ball 90. Chamber 92 includes a peripheral chamber wall 110 having a cylindrical wall portion 112 extending along a cylindrical axis 114 between a first end wall portion 116, juxtaposed with the pole 100 of the ball 90, and a second end wall portion 118, juxtaposed with the pole 102 of the ball 90. Air inlet passages 120 provide air inlets 122 to the chamber 92, the inlet passages 120 communicating with a manifold 124 which itself communicates with an inlet port 126 in the housing 86. Air outlet passages 130 and 132 provide first and second air outlets 134 and 136, respectively, the outlet passage 130 communicating with an exhaust port 140 in the housing 86 and the outlet passage 132 communicating with an exhaust port 142 in the housing 86.

As seen in FIGS. 1 and 2, with reference to FIGS. 3 and 4, air under pressure supplied at nipple 24 passes through rear air feed passage 40 and intermediate air feed passage 46 to forward air feed passage 56 to be admitted into chamber 92 through inlet port 126, manifold 124, inlet passages 120 and inlets 122. Air which is admitted into the chamber 92 through inlets 122 is exhausted from the chamber 92 to the interior 74 of the forward tubular segment 30 through outlets 134 and 136, outlet passages 130 and 132 and exhaust ports 140 and 142. Air exhausted into the interior 74 then is passed to the ambient atmosphere through forward exhaust passages 150 in the coupling member 34 and rearward exhaust passages 42 in the rear fitting 36, the bore 70 being sealed against the escape of air by ring 68.

Air under pressure admitted to chamber 92 and then exhausted from chamber 92 causes ball 90 to rotate within the chamber 92, thereby inducing vibratory motion in housing 82, which vibratory motion is transmitted to forward fitting 50 by virtue of the coupling means provided by the securement of the housing 82 within the forward fitting 50. Forward fitting 50, being coupled to the scaling tool 22 and being suspended within the forward tubular segment 30 by the tubular coupling member 54 and the ring 68, which serve as resilient support means for supporting the vibratory transducer 80 within the housing 12, transmits vibratory motion to the scaling tool 22, while being essentially isolated from transmitting undue vibration to the finger grip portion 20 of housing 12. The relative dimensions of the diameter D of the ball 90 and the peripheral wall 110 of the chamber 92 provides a relatively small clearance between the ball 90 and the peripheral wall 110, enabling very high speed rotation of the ball 90 within the chamber 92 and the concomitant transmission of high frequency, low amplitude vibrational energy to the housing 82 and, consequently, to the scaling tool 22. In a typical dental scaler 10, a ball 90 having a diameter D of about three-thirty-seconds of an inch rotates within a chamber 92 having a cylindrical diameter 94 greater than the diameter D of the ball 90 so that the small clearance between the ball 90 and the peripheral wall 110 of the chamber 74 is about one-sixty-fourth of an inch. With air under a pressure of about 40 to 45 psi, the vibratory motion transmitted to the scaling tool 22 is within a high sonic to supersonic range, typically about 18,000 Hz, at a relatively low amplitude.

Figure 5:
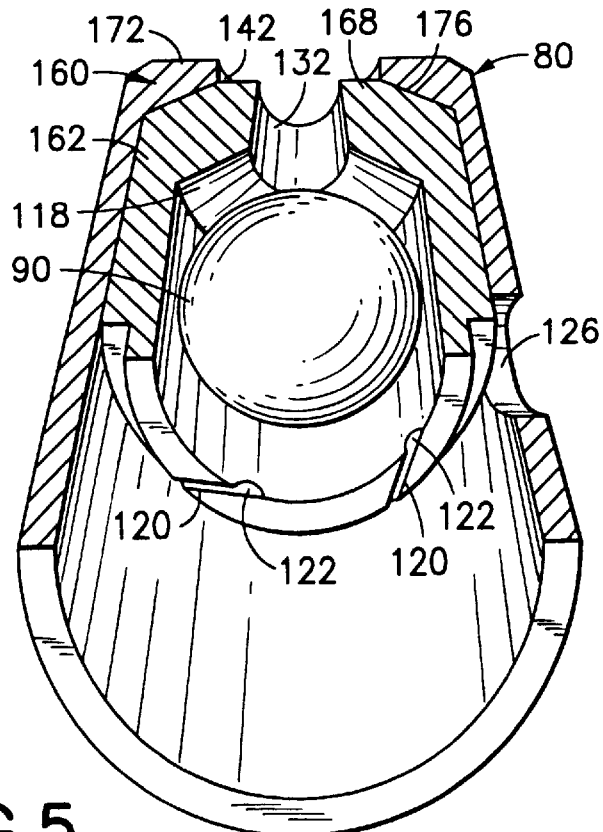
FIG. 5 is a fragmentary perspective view showing a portion of the vibratory transducer.

In the preferred construction illustrated in FIGS. 3 through 5, housing 82 of the vibratory transducer 80 is in the form of a metallic shell 160 within which there is placed a cup-shaped chamber member 162 and a closure member 164. Chamber member 162 includes a cylindrical wall 166 which extends along cylindrical axis 114 between an end wall 168 and an opposite end 170 and is seated within shell 160, against a flange 172 of the shell 160. Ball 90 preferably is a solid metallic ball, the preferred material for the ball 90 being a high grade steel, and is located within the chamber member 162, as seen in FIG. 5, and the closure member 164 is inserted into the shell 160 and seated against the chamber member 162. Then, the shell 160 is deformed over the closure member 164 to establish a retaining lip 174 which secures together the assembled shell 160, chamber member 162 and closure member 164. Tapers at 176 and 178 facilitate the assembly and securement of the component parts, as described.

The air inlet passages 120 are located at the end 170 of the chamber member 162, placing the air inlets 122 at the first end 96 of the chamber 92, juxtaposed with the pole 100 of the ball 90. The placement of the air inlets 122 at an end of the chamber 92, juxtaposed with a pole of the ball 90, together with the relatively small clearance between the ball 90 and the wall of the chamber 92 enables the high speed rotation of the ball 90 which attains the desired high frequency and low amplitude vibratory motion. The air inlets 122 thus are positioned so that the air inlets 122 remain unobstructed by the ball 90, regardless of the position of the ball 90 within the chamber 92. Since the air inlets 122 are positioned for the unobstructed flow of air into the chamber 92 during operation of the vibratory transducer 80, the air inlets 122 may be made relatively small for the passage of relatively fine streams of air at high velocity. Typically, the air inlets have a diameter of about one-sixty-fourth of an inch and the air exhaust outlets have a diameter of about one-thirty-second of an inch.

As best seen in FIGS. 3 through 5, the air inlet passages 120 lie in a radial plane 180 and extend along directions 182 spaced radially from the cylindrical axis 114 of the chamber 92, the directions 182 preferably being generally tangential to the cylindrical wall portion 112 of the chamber wall 110 so that the air admitted to the chamber 92 is best directed for inducing rotation in the ball 90. It is desirable to provide at least two air inlet passages 120, and the preferred number of air inlet passages 120 is four, with the air inlet passages 120 being spaced circumferentially around the chamber wall 110 equidistant from one another, as shown. In the preferred arrangement, two air outlet passages 130 and 132 are provided and both air passages 130 and 132 are aligned with the cylindrical axis 114 of the wall portion 112 of chamber wall 110. When in the preferred alignment, the provision of two air outlet passages 130 and 132 assures that at least one air passage 130 or 132 is always open for the exhaust of air admitted to the chamber 92, regardless of the position of the ball 90 in the chamber 92 during operation of the vibratory transducer 80.

Figure 6:
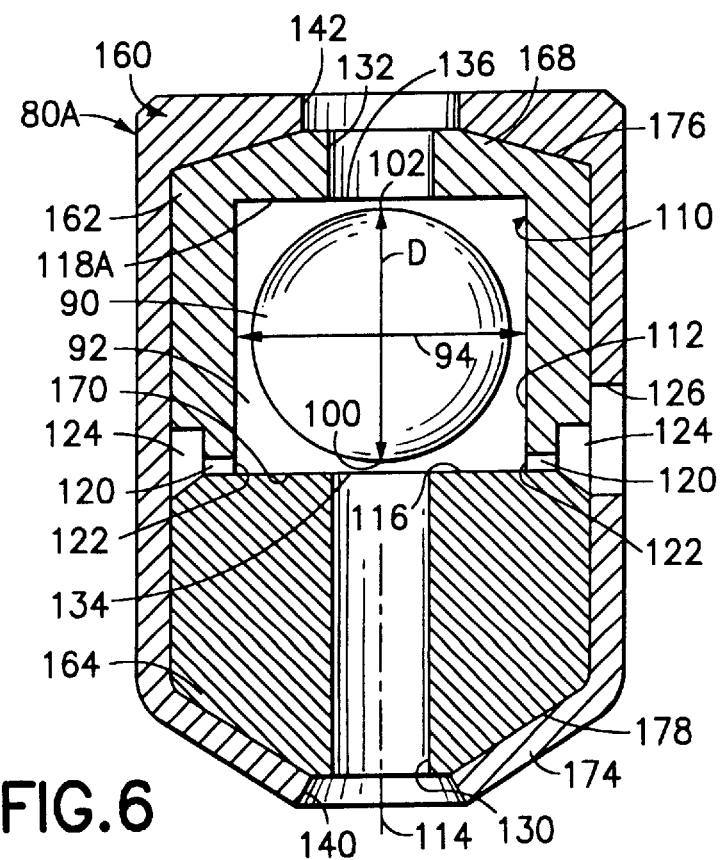
FIG. 6 is a longitudinal cross-sectional view similar to FIG. 3, and showing another embodiment of the invention.

It has been found that performance of the vibratory transducer 80 is enhanced by providing the second end wall portion 118 with a taper such that the second end wall portion 118 is tapered from the cylindrical wall portion 112 toward the outlet 136 at an angle A to the cylindrical axis 114 and, consequently, to the polar axis P of the ball 90, as seen in FIG. 3. The preferred magnitude of angle A is about 60°. However, in an alternate embodiment of vibratory transducer 80, illustrated at 80A in FIG. 6, wherein component parts corresponding to counterpart component parts illustrated in FIG. 3 are labelled with the same reference characters, end wall portion 118A is normal to the cylindrical axis 114, and to the polar axis P, and operation of the vibratory transducer 80A is satisfactory.

The relative dimensions of the ball 90 and interior dimensions of the chamber 92 are such that a relatively small amount of clearance is provided between the ball 90 and the peripheral chamber wall 110, as described above, thereby attaining relatively high frequency, low amplitude vibratory motion for transmitting the desired high frequency, low amplitude vibratory energy. In the illustrated preferred embodiment, the vibratory transducer 80 is oriented within the housing 12 so that the cylindrical axis 114 of the cylindrical wall portion 112 of chamber 92 and, consequently, the polar axis P of ball 90, extend transverse to the longitudinal axis L of the housing 12, with the cylindrical axis 114 and the polar axis P preferably being normal to the longitudinal axis L.

Figure 7:
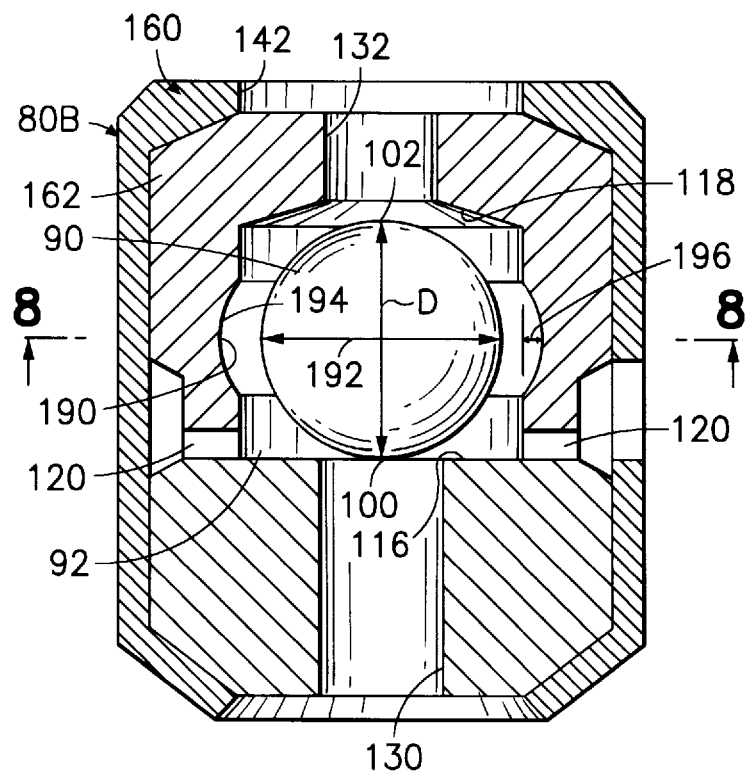
FIG. 7 is a longitudinal cross-sectional view similar to FIG. 3, and showing still another embodiment of the invention.
Figure 8:
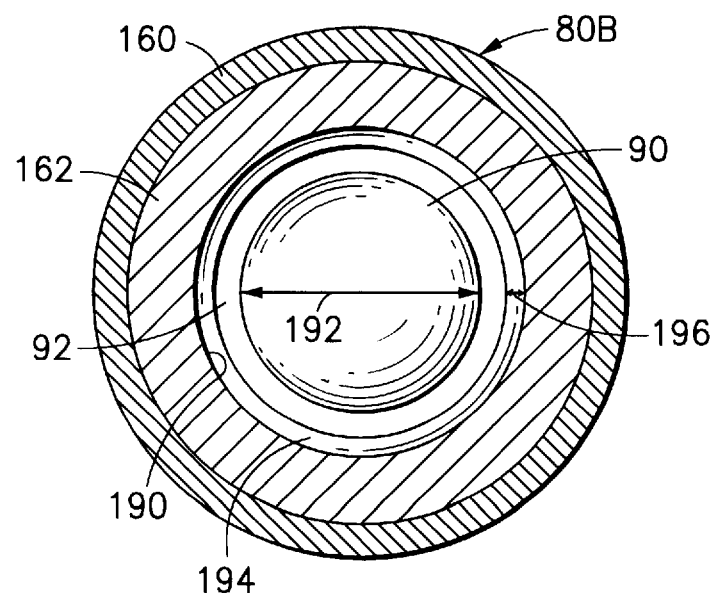
FIG. 8 is a cross-sectional view taken along line 8—8 of FIG. 7.

Another embodiment of the invention is illustrated as alternate transducer 80B in FIGS. 7 and 8, wherein component parts corresponding to counterpart component parts illustrated in FIGS. 3 and 4 are labelled with the same reference characters. The performance of transducer 80B is further enhanced by the provision of a race within which ball 90 rotates within the chamber 92, the race being shown in the form of an annular groove 190 in the chamber member 162. Ball 90 has an equator 192 intermediate the opposite poles 100 and 102 of the ball 90 and annular groove 190 has an arcuate profile contour 194 essentially complementary to the surface contour of the ball 90 at the equator 192 and is juxtaposed with the ball 90 at the equator 192. Annular groove 190 is located intermediate the end wall portions 116 and 118 so as to guide the ball 90 for rotation along a circular path defined by the annular groove 190, the groove 190 being spaced from both the end wall portions 116 and 118 such that rotation of the ball 90 along the circular path within the chamber 92 is accomplished smoothly and effectively, along a path spaced from the end wall portions 116 and 118 so as to maintain the ball 90 spaced from the end wall portions 116 and 118 and thereby deter deleterious impingement of the ball 90 against the end wall portions 116 and 118 during operation of the transducer 80B. In the preferred construction where ball 90 has a diameter of about three-thirty-seconds of an inch, a groove 190 having a depth 196 of about one-sixty-fourth of an inch has demonstrated exemplary performance.

It will be seen that the present invention attains the several objects and advantages summarized above, namely: Provides an air-driven vibratory dental scaler which is capable of operating at frequencies significantly higher than those attained by my earlier dental scalers; enables operation of a dental scaler at low amplitudes of vibration, with increased power; operates at lower noise levels than my earlier dental scalers; provides an instrument which is compact and is relatively simple in design and construction; provides a dental scaler which is more efficient in use and is more comfortable from the standpoint of both the dental operator and the patient; provides a vibratory transducer for use in various other implements for enabling the construction of more effective implements; enables the construction of a vibratory transducer of simplified and economical construction.

It is to be understood that the above detailed description of preferred embodiments of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A dental scaler having a scaling tool to be vibrated at a high frequency and low amplitude by a fluid under pressure, the dental scaler comprising:

an outer tubular housing extending along a longitudinal axis between opposite ends;

a vibratory transducer within the outer tubular housing;

coupling means for coupling the scaling tool to the vibratory transducer;

resilient support means for supporting the vibratory transducer within the outer tubular housing;

the vibratory transducer comprising:

an inner housing having a chamber including a peripheral wall extending between opposite first and second chamber ends;

an essentially spherical rotor within the chamber, the rotor having a diameter, a polar axis extending along the diameter between opposite poles, and an equator intermediate the opposite poles;

a race in the peripheral wall of the chamber, the race being located intermediate the first and second chamber ends and juxtaposed with the equator of the rotor;

at least two fluid inlets located adjacent the first chamber end and juxtaposed with one of the opposite poles of the rotor for admitting the fluid under pressure into the chamber and directing the fluid toward the rotor adjacent the one of the opposite poles; and at least one fluid outlet aligned essentially with the polar axis of the rotor for exhausting from the chamber the fluid admitted into the chamber;

the relative dimensions of the peripheral wall of the chamber and the diameter of the rotor providing a relatively small clearance between the rotor and the peripheral wall of the chamber for enabling relatively high speed rotation of the rotor within the race in the chamber, in response to the passage of the fluid under pressure through the inlets into the chamber and through the outlet out of the chamber, and the concomitant transmission of relatively high frequency, low amplitude vibrational energy from the rotating rotor to the inner housing and to the scaling tool.

2. The invention of claim 1 wherein the chamber includes two outlets located such that one outlet is placed at each of the first and second chamber ends, juxtaposed with a corresponding one of the poles of the rotor.

3. The invention of claim 1 wherein the peripheral wall of the chamber includes a generally cylindrical wall portion having a cylindrical axis aligned with the polar axis of the rotor and the race includes an annular groove in the generally cylindrical wall portion.

4. The invention of claim 3 wherein the peripheral wall of the chamber includes opposite first and second end wall portions located at respective ones of the opposite first and second chamber ends, the chamber includes two outlets located such that one outlet is placed at each of the first and second end wall portions, juxtaposed with a corresponding one of the poles of the rotor, and the annular groove is spaced from each of the first and second end wall portions so as to guide the rotor along a path which maintains the rotor spaced from the first and second end wall portions during rotation of the rotor in the race in the chamber.

5. The invention of claim 4 wherein the second end wall portion is tapered from the cylindrical wall portion toward the outlet in the second end wall portion.

6. The invention of claim 5 wherein the second end wall is tapered at about 60° to the polar axis of the rotor.

7. The invention of claim 4 wherein the inlets include inlet passages directed along directions spaced radially from the polar axis of the rotor.

8. The invention of claim 7 wherein the directions along which the inlet passages are directed lie in a radial plane and are generally tangential to the cylindrical wall portion of the chamber.

9. The invention of claim 4 including four inlets spaced circumferentially around the chamber equidistant to one another.

10. The invention of claim 9 wherein the inlets include inlet passages directed along directions spaced radially from the polar axis of the rotor.

11. The invention of claim 10 wherein the directions along which the inlet passages are directed lie in a radial plane and are generally tangential to the cylindrical wall portion of the chamber.

12. The invention of claim 1 wherein the polar axis of the rotor extends transverse to the longitudinal axis of the outer tubular housing.

13. The invention of claim 12 wherein the polar axis of the rotor is normal to the longitudinal axis of the outer tubular housing.

14. The invention of claim 1 wherein the rotor comprises a solid metallic ball.

15. A vibratory transducer for providing high frequency, low amplitude vibrational energy in response to a fluid under pressure, the vibratory transducer comprising:

a housing having a chamber including a peripheral wall extending between opposite first and second chamber ends;

an essentially spherical rotor within the chamber, the rotor having a diameter, a polar axis extending along the diameter between opposite poles, and an equator intermediate the opposite poles;

a race in the peripheral wall of the chamber, the race being located intermediate the first and second chamber ends and juxtaposed with the equator of the rotor;

at least two fluid inlets located adjacent the first chamber end and juxtaposed with one of the opposite poles of the rotor for admitting the fluid under pressure into the chamber and directing the fluid toward the rotor adjacent the one of the opposite poles; and at least one fluid outlet aligned essentially with the polar axis of the rotor for exhausting from the chamber the fluid admitted into the chamber;

the relative dimensions of the peripheral wall of the chamber and the diameter of the rotor providing a relatively small clearance between the rotor and the peripheral wall of the chamber for enabling relatively high speed rotation of the rotor within the race in the chamber, in response to the passage of the fluid under pressure through the inlets into the chamber and through the outlet out of the chamber, and the concomitant transmission of relatively high frequency, low amplitude vibrational energy from the rotating rotor to the housing.

16. The invention of claim 15 wherein the chamber includes two outlets located such that one outlet is placed at each of the first and second chamber ends, juxtaposed with a corresponding one of the poles of the rotor.

17. The invention of claim 15 wherein the peripheral wall of the chamber includes a generally cylindrical wall portion having a cylindrical axis aligned with the polar axis of the rotor and the race includes an annular groove in the generally cylindrical wall portion.

18. The invention of claim 17 wherein the peripheral wall of the chamber includes opposite first and second end wall portions located at respective ones of the opposite first and second chamber ends, and the chamber includes two outlets located such that one outlet is placed at each of the first and second end wall portions, juxtaposed with a corresponding one of the poles of the rotor, and the annular groove is spaced from each of the first and second end wall portions so as to guide the rotor along a path which maintains the rotor spaced from the first and second end wall portions during rotation of the rotor in the race in the chamber.

19. The invention of claim 18 wherein the second end wall portion is tapered from the cylindrical wall portion toward the outlet in the second end wall portion.

20. The invention of claim 19 wherein the second end wall is tapered at about 60° to the polar axis of the rotor.

21. The invention of claim 18 wherein the inlets include inlet passages directed along directions spaced radially from the polar axis of the rotor.

22. The invention of claim 21 wherein the directions along which the inlet passages are directed lie in a radial plane and are generally tangential to the cylindrical wall portion of the chamber.

23. The invention of claim 18 including four inlets spaced circumferentially around the chamber equidistant to one another.

24. The invention of claim 23 wherein the inlets include inlet passages directed along directions spaced radially from the polar axis of the rotor.

25. The invention of claim 24 wherein the directions along which the inlet passages are directed lie in a radial plane and are generally tangential to the cylindrical wall portion of the chamber.

26. The invention of claim 15 wherein the rotor comprises a solid metallic ball.

* * * * *